United States Patent [19]
Clement, Jr. et al.

[11] Patent Number: 5,746,771
[45] Date of Patent: May 5, 1998

[54] CALCAR COLLAR INSTRUMENTATION

[75] Inventors: Lemuel Vance Clement, Jr.; Joseph S. Clift, Jr., both of Memphis; Rodney L. Houfburg, Cordova, all of Tenn.

[73] Assignee: Wright Medical Technology, Inc., Arlington, Tenn.

[21] Appl. No.: 723,992

[22] Filed: Sep. 30, 1996

[51] Int. Cl.⁶ ........................................ A61F 2/28
[52] U.S. Cl. .................................................. 623/16
[58] Field of Search ............................ 623/16, 18, 19, 623/22, 23

[56] References Cited

U.S. PATENT DOCUMENTS

| | | |
|---|---|---|
| 4,601,289 | 7/1986 | Chiarizzio et al. . |
| 4,698,063 | 10/1987 | Link et al. . |
| 4,770,660 | 9/1988 | Averill . |
| 4,908,036 | 3/1990 | Link et al. . |
| 5,100,407 | 3/1992 | Conrad et al. . |
| 5,108,452 | 4/1992 | Fallin . |

*Primary Examiner*—David Isabella
*Attorney, Agent, or Firm*—Walker, McKenzie & Walker, P.C.

[57] ABSTRACT

Calcar collar instrumentation including a calcar collar and a proximal femoral stem. The calcar collar includes a foot with a foot member having a face surface; a back attached to the foot and including a back member having a face surface arranged at an angle to the face surface of the foot member; and attachment structure for removably and adjustably attaching the foot and the back to the proximal femoral stem. The proximal femoral stem includes one or more necks for allowing the calcar collar to be snapped thereto.

9 Claims, 5 Drawing Sheets

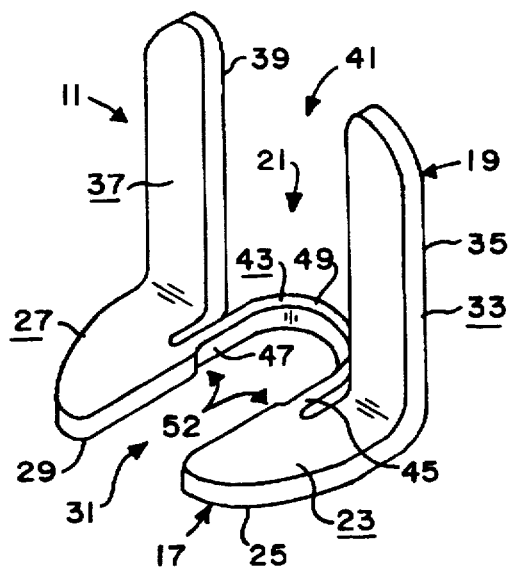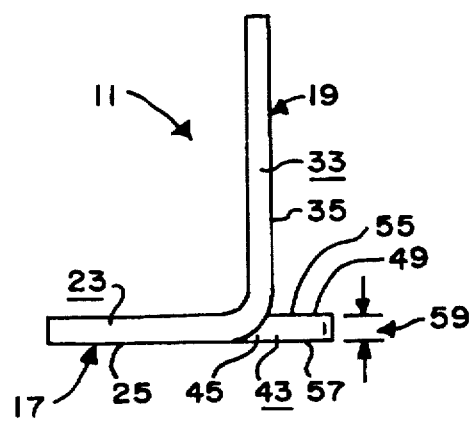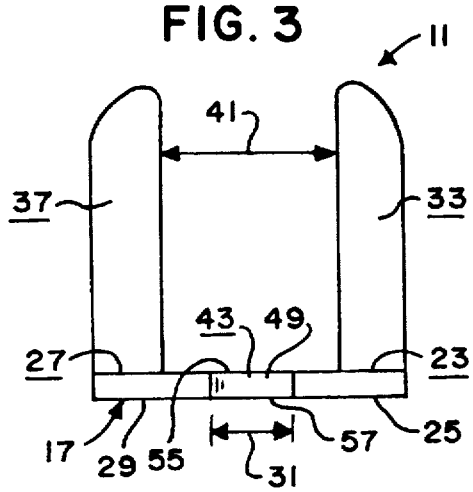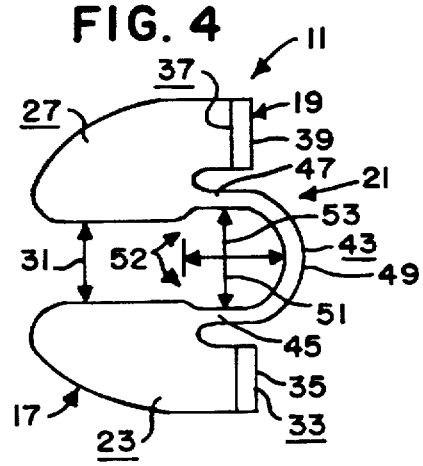

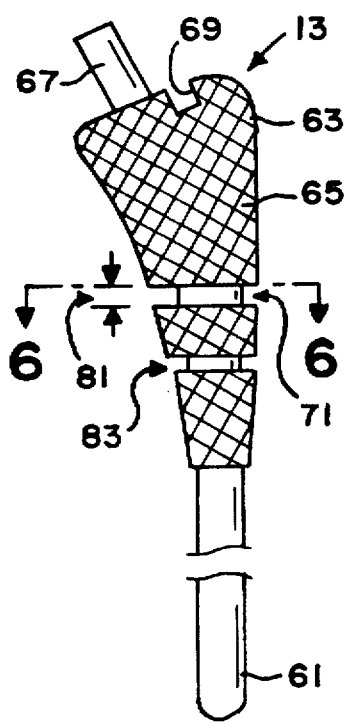
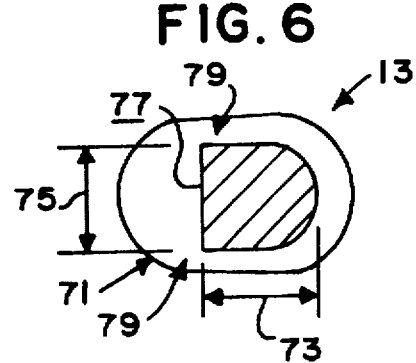
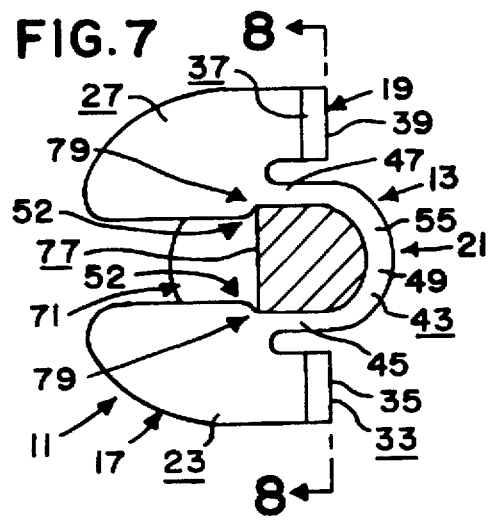
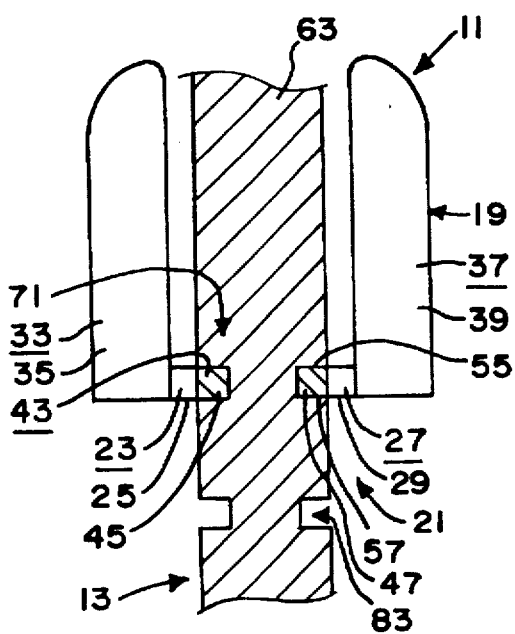

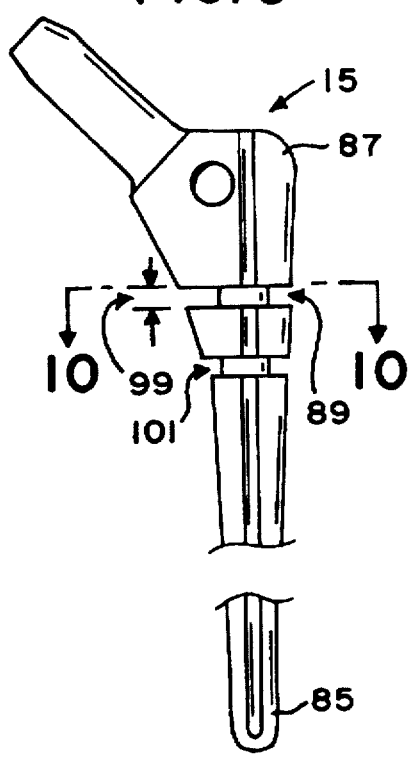
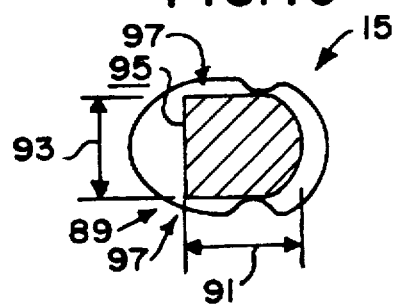
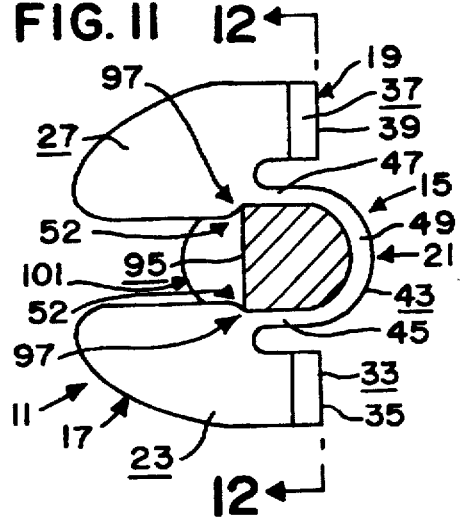
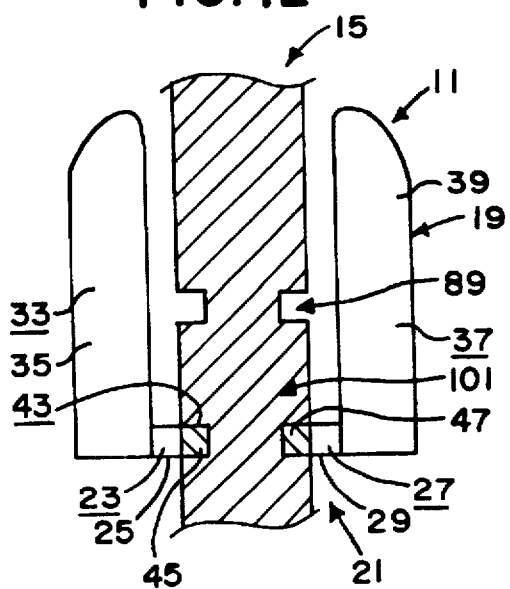

CALCAR COLLAR INSTRUMENTATION

BACKGROUND OF THE INVENTION

1. Field of the Invention

The present invention relates, in general, to instrumentation for preparing a proximal femur for trial reduction, and instrumentation for use in such a trial reduction.

2. Information Disclosure Statement

A preliminary patentability search produced the following patents which appear to be relevant to the present invention:

Chiarizzio et al., U.S. Pat. No. 4,601,289, issued Jul. 22, 1986, discloses a femoral trial prosthesis/rasp assembly for use in hip implant surgery. A handle assembly grips a combination trial prosthesis/rasp in a secure manner by clamping over and locking onto a post on the trial prosthesis/rasp which later serves as a mounting piece for a femoral prosthesis head used in trial reductions.

Link et al., U.S. Pat. No. 4,698,063, issued Oct. 6, 1987, discloses a femoral hip-joint prosthesis comprising a head part, a stem to be anchored in the bone, and a support collar terminating the stem at the head end. In order to make it easy for the surgeon, on reoperation, to remove the prosthesis stem from the bone tissue, the support collar can be removed from the stem. In addition, the support collar can be combined with an anchor for attachment to the greater trochanter.

Averill, U.S. Pat. No. 4,770,660, issued Sep. 13, 1988, discloses a stem-type femoral prosthesis having a calcar collar that can be selectively installed on the stem or removed from the stem interoperatively by sliding the collar in transverse directions between the medial and lateral sides of the stem, to facilitate seating of the stem without the collar during implantation of the stem, and to enable subsequent removal of the stem by first removing the collar from the stem to gain access to the affixed surfaces of the stem beneath the collar.

Link et al., U.S. Pat. No. 4,908,036, issued Mar. 13, 1990, discloses an endoprosthesis having a stem to be anchored in bone, and a separate bone support. The bone support is attached to the stem in a manner that is pivotable, and preferably spherically mobile, so that it adjusts itself automatically to the position of the bone surface that supports it.

Conrad et al., U.S. Pat. No. 5,100,407, issued Mar. 31, 1992, discloses a modular trial hip replacement system including at lest three trial stem portions of different sizes, and at least three trial body portions of different sizes. The stem and body portions include mating male and female elements which allow the stem portions to be securely coupled to the body portions. Each body portion includes two generally perpendicular guide surfaces which serve to guide the saw blade used by the surgeon during the resecting of the head/neck area of the femur or to be used to check a free-hand cut.

Fallin, U.S. Pat. No. 5,108,452, issued Apr. 28, 1992, discloses a modular hip prosthesis including a body having a neck portion for carrying a rounded head element, a transitional mid-section, and a stem section. Removable collars can be added to the transitional mid-section of the body of the prosthesis to form a transverse load carrying interface with the upper end of the patient's femur.

Nothing in the known prior art discloses or suggests the present invention. More specifically, nothing in the known prior art discloses or suggests calcar collar instrumentation including a calcar collar having a foot member with a face surface; a back member attached to the foot member and having a face surface arranged at an angle to the face surface of the foot member; and attachment means for removably and adjustably attaching the foot member and the back member to a proximal femoral stem that includes one or more necks for allowing the calcar collar to be attached thereto.

SUMMARY OF THE INVENTION

The present invention provides calcar collar instrumentation that includes a calcar collar having a foot member with a face surface; a back member attached to the foot member and having a face surface arranged at an angle to the face surface of the foot member; and attachment means for removably and adjustably attaching the foot member and the back member to a proximal femoral stem that includes one or more necks for allowing the calcar collar to be attached thereto.

The present invention provides a calcar collar for attachment to a proximal femoral stem to act as a guide and stop for the insertion of the proximal femoral stem. The calcar collar may approximate the size and location of an actual implant's calcar collar. The calcar collar may be snapped onto different levels on the proximal femoral stem to account for all combinations of available actual implants. The calcar collar is held in place by the inherent spring properties of its design and base material. The calcar collar includes face portions in both the sagittal plane and the transverse plane, which may mimic the actual implant configuration. The proximal femoral stem may consist of a combined toothed rasp/trial or a dedicated trial, etc. The calcar collar, when attached to a rasp, can be used as a reference or guide in making the femoral cuts necessary to insert the actual implant, and as a physical stop that indicates the femur has been broached or rasped to the appropriate depth.

One object of the present invention is to provide calcar collar instrumentation that functions as a stop to indicate that a femur has been broached to an appropriate depth and/or to indicate that a trial stem has been inserted to an appropriate depth.

Another object of the present invention is to provide calcar collar instrumentation that functions as a reference to guide the insertion of a rasp and/or trial into a proximal femur.

Another object of the present invention is to provide modular calcar collar instrumentation that can be adjusted to approximate the size and design of a plurality of permanent proximal femoral prostheses of various sizes and designs.

Another object of the present invention is to provide an interchangeable calcar collar for allowing implant size and fit to be assessed while evaluating range of motion prior to final implant selection and implantation.

BRIEF DESCRIPTION OF THE DRAWINGS

FIG. 1 is a perspective view of a calcar collar of the present invention.

FIG. 2 is a front elevational view of the calcar collar of FIG. 1.

FIG. 3 is a side elevational view of the calcar collar of FIG. 1.

FIG. 4 is a top plan view of the calcar collar of FIG. 1.

FIG. 5 is a front elevational view of a combined proximal femoral rasp/trial stem of the present invention.

FIG. 6 is a sectional view substantially as taken on line 6—6 of FIG. 5, shown somewhat enlarged with respect to FIG. 5.

3

FIG. 7 is a sectional view similar to FIG. 6 but showing the calcar collar of FIG. 1 attached to the proximal femoral rasp/trial stem thereof.

FIG. 8 is a sectional view substantially as taken on line 8—8 of FIG. 7.

FIG. 9 is a front elevational view of a proximal femoral trial stem of the present invention.

FIG. 10 is a is a sectional view substantially as taken on line 10—10 of FIG. 9, shown somewhat enlarged with respect to FIG. 9.

FIG. 11 is a sectional view similar to FIG. 10 but showing the calcar collar of FIG. 1 attached to the proximal femoral trial stem thereof.

FIG. 12 is a sectional view substantially as taken on line 12—12 of FIG. 11.

Figure 13:
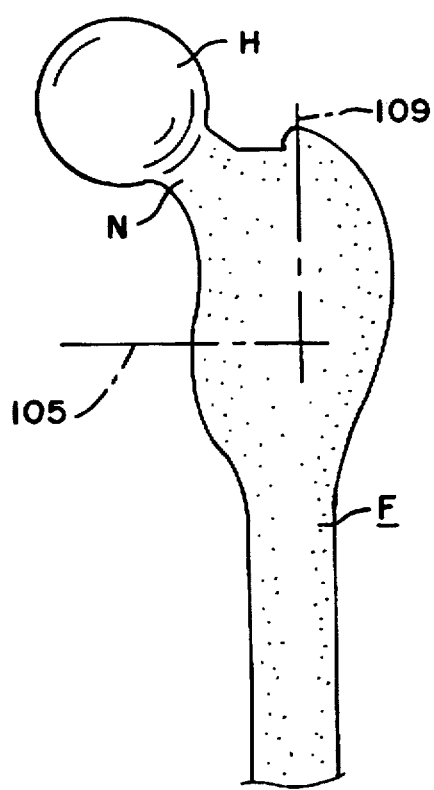

FIG. 13 is a front elevational view of a proximal femur.

Figure 14:
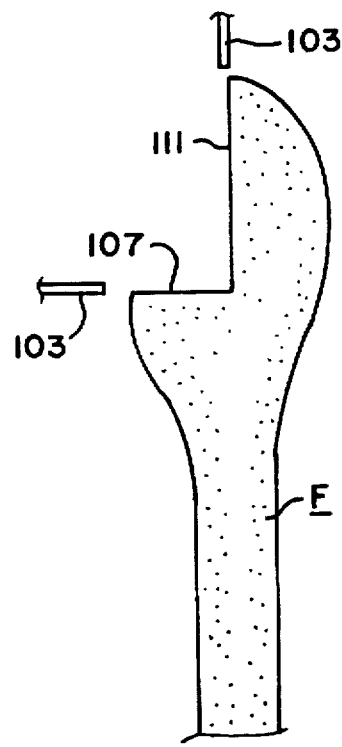

FIG. 14 is a front elevational view of the proximal femur of FIG. 13 but showing transverse and sagittal resections thereof.

Figure 15:
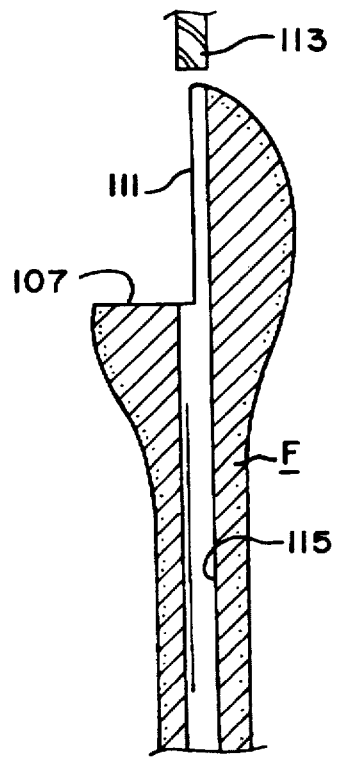

FIG. 15 is a sectional view of the femur of FIG. 14 but showing an intramedullary bore therein.

Figure 16:
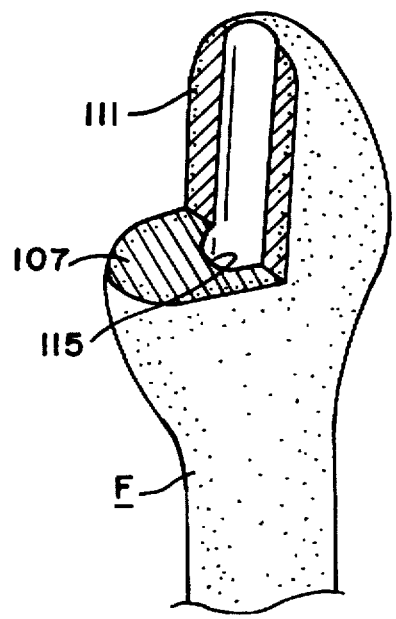

FIG. 16 is a perspective view of the proximal femur of FIG. 15.

Figure 17:
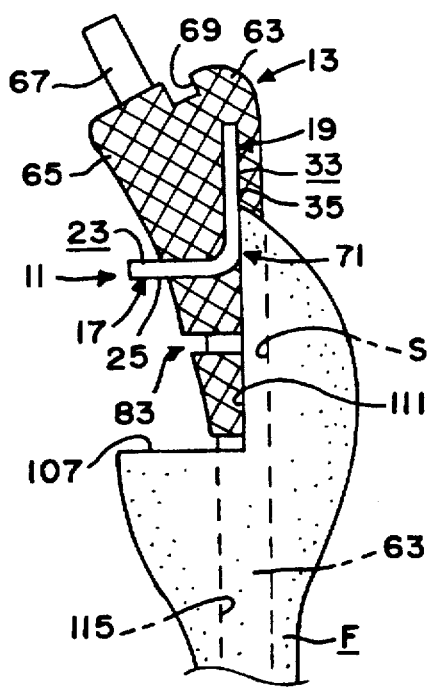

FIG. 17 shows the calcar collar of FIG. 1 and the proximal femoral rasp/trial stem of FIG. 5 combined with one another and partially inserted into a partially prepared proximal femur.

Figure 18:
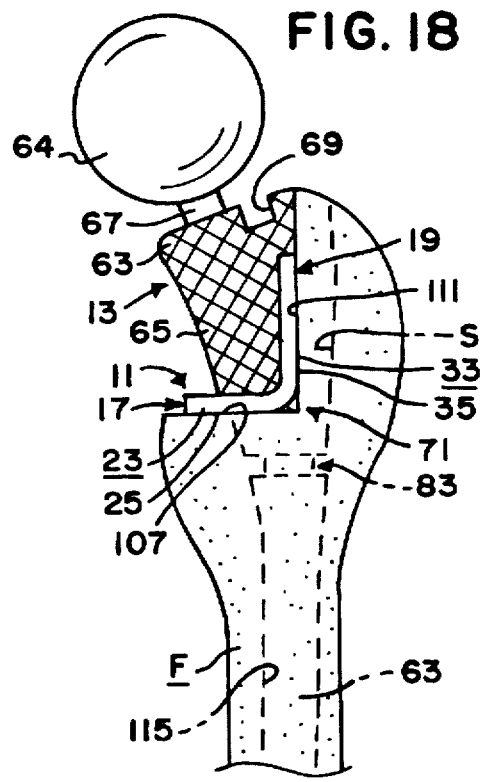

FIG. 18 shows the calcar collar of FIG. 1 and the proximal femoral rasp/trial stem of FIG. 5 combined with one another and with a proximal femoral trial head, and fully inserted into the proximal femur.

Figure 19:
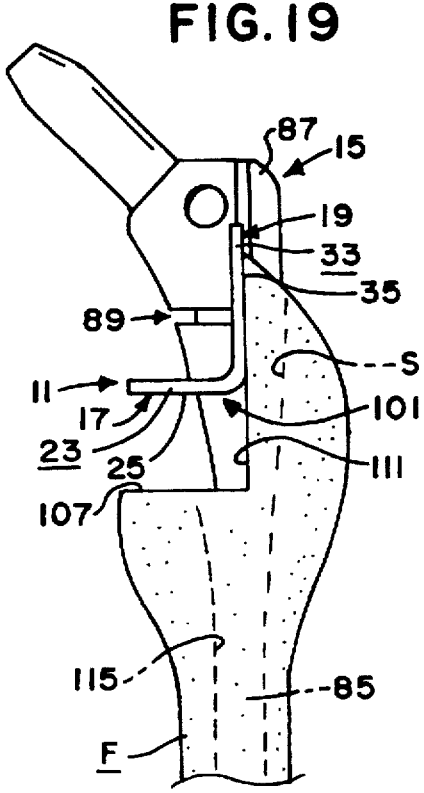

FIG. 19 shows the calcar collar of FIG. 1 and the proximal femoral trial stem of FIG. 9 combined with one another, and partially inserted into a prepared proximal femur.

Figure 20:
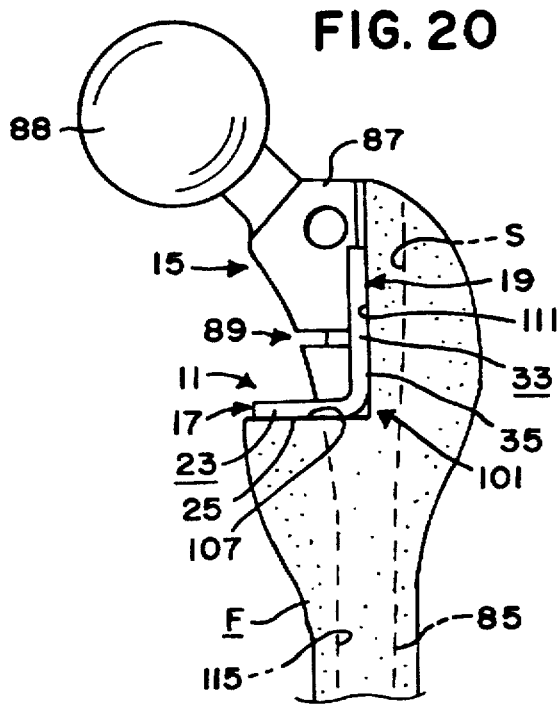

FIG. 20 shows the calcar collar of FIG. 1 and the proximal femoral trial stem of FIG. 9 combined with one another and with a proximal femoral trial head, and fully inserted into the proximal femur.

DESCRIPTION OF THE PREFERRED EMBODIMENTS

Preferred embodiments of various components of the calcar collar instrumentation of the present invention are shown in FIGS. 1–12 and 17–20. The calcar collar instrumentation of the present invention includes, in general, a calcar collar 11 and a proximal femoral stem. The proximal femoral stem may include or consist of a proximal femoral rasp (not shown) for preparing a socket S in a proximal femur F to receive a trial proximal femoral prosthesis and a permanent proximal prosthesis; a combined proximal femoral rasp/trial stem 13 (see FIGS. 5–8, 17 and 18) for preparing a socket S in a proximal femur F to receive a permanent proximal femoral prosthesis and for allowing a trial reduction of that proximal femur F; a proximal femoral trial stem 15 (see FIGS. 9–12, 19 and 20) for insertion into a prepared socket S in a proximal femur F to allow a trial reduction of that proximal femur F, etc.

The calcar collar 11 includes a foot 17, a back 19 attached to the foot 17, and an attachment means 21 for removably and adjustably attaching the foot 17 and back 19 to a proximal femoral stem (e.g., to the combined proximal femoral rasp/trial stem 13 or to the proximal femoral trial stem 15).

The foot 17 includes a foot member having a face surface. More specifically, the foot 17 preferably includes a first foot member 23 having a face surface 25, and a second foot member 27 having a face surface 29. The first and second foot members 23, 27 are preferably spaced apart from one another to form a first gap 31 therebetween (see, in general, FIGS. 1, 3 and 4). The face surfaces 25, 29 of the first and second foot members 23, 27 are preferably planar. The outer end of each foot member 23, 27 may be rounded as clearly shown in the drawings to generally correspond with the curvature of the medial edge of a transverse section through a proximal femur F.

The back 19 includes a back member having a face surface. More specifically, the back 19 preferably includes a first back member 33 having a face surface 35, and a second back member 37 having a face surface 39. The first and second back members 33, 37 are attached to the first and second foot members 23, 27, respectively, with the face surfaces 35, 39 of the back members 33, 37 arranged at an angle to the face surfaces 25, 29 of the respective foot members 23, 27. The face surfaces 35, 39 of the first and second back members 33, 35 are preferably planar and arranged substantially at right angles to the planar face surfaces 25, 29 of the respective foot members 23, 27. The first and second back members 33, 37 are preferably spaced apart from one another to form a second gap 41 therebetween (see, in general, FIGS. 1 and 3). The outer end of each back member 33, 37 may be rounded as clearly shown in the drawings to generally correspond with the curvature of the proximal edge of a sagittal section through a proximal femur F.

The calcar collar 11 preferably includes a link 43 joining the first and second foot members 23, 27 together. The link 43 preferably includes a first end 45 joined relative to the first foot member 23, a second end 47 joined relative to the second foot member 27, and a bight portion 49 extending between the first and second ends 45, 47 thereof. The first and second ends 45, 47 of the link 43 are preferably spaced apart from one another to form a third gap 51 (see FIG. 4). The third gap 51 is preferably wider than the first gap 31 so that corners 52 (see FIG. 4) are formed at the junction between the first and second foot members 23, 27 and the first and second ends 45, 47, respectively. The bight portion 49 preferably extends from the first and second ends 45, 47 of the link 43 to form a fourth gap 53 (see FIG. 4). The link 43 preferably has a first face 55 and a second face 57 that are spaced apart from one another a set distance 59 (see FIG. 2). The bight portion 49 of the link 43 is preferably curved in a semicircle or the like, and preferably has an elastic quality so that it can recover its shape after being bent or stretched to thereby give the calcar collar 11 inherent spring properties to removably and adjustably attaching the foot 17 and back 19 to the proximal femoral stem in a manner and for reasons which will hereinafter become apparent. Thus, the attachment means 21 is created or defined, at least in part, by the link 43.

The calcar collar 11 may be constructed in various manners and out of various materials as will now be apparent to those skilled in the art. Thus, for example, the calcar collar 11 is preferably forged, machined or otherwise constructed as a one-piece, integral unit out of a medical grade, physiologically acceptable metal such as stainless steel or the like, in various sizes to fit a range of typical patients and in various specific ornamental designs, etc.

The proximal femoral rasp/trial stem 13 may be substantially similar to any typical proximal femoral rasp/trial stem well known to those skilled in the art, such as the combined trial prosthesis/rasp 602 disclosed generally at columns 3–5 and in FIGS. 6 and 7 of Chiarizzio et al., U.S. Pat. No.

4,601,289, issued Jul. 22, 1986, incorporated herein by reference. Thus, the proximal femoral rasp/trial stem 13 incudes a first end 61 for inserting into the proximal femur F, a second end 63 to which a proximal femoral trial head 64 can be attached (see FIG. 18) to perform a trial reduction of a hip joint, and cutting means 65 on at least a portion of the exterior thereof for shaping and enlarging the socket S in the proximal femur F as will now be apparent to those skilled in the art. The cutting means 65 may consist of teeth or the like provided in or on a portion of the exterior of the proximal femoral rasp/trial stem 13 in a shape and size that matches the shape and size of the socket S desired to form in proximal femur F as will now be apparent to those skilled in the art. The proximal femoral rasp/trial stem 13 preferably includes connection means such as a post 67 and recess 69 on the second end 63 thereof (generally corresponding to the post 604 and recess 700 of the trial prosthesis/rasp 602 disclosed in the above referenced Chiarizzio et al., U.S. Pat. No. 4,601,289) to allow a handle assembly (not shown), such as the handle assembly 100 disclosed in the above referenced Chiarizzio et al., U.S. Pat. No. 4,601,289, to be securely connected thereto as will now be apparent to those skilled in the art.

However, the proximal femoral rasp/trial stem 13 includes certain improvements to such a typical proximal femoral rasp/trial stem, and is especially designed and constructed for use in combination with the calcar collar 11. More specifically, the proximal femoral rasp/trial stem 13 has a first groove or neck 71 adjacent the second end 63 thereof for receiving the calcar collar 11. The first neck 71 has a cross-sectional shape and has a certain depth 73 and width 75 as clearly shown in FIG. 6. The width of the third gap 51 between the first and second ends 45, 47 of the link 43 is at least equal to the width 75 of the of the first neck 71, and is preferably the same as the width 75, plus a small tolerance dimension, for allowing the first neck 71 to fit between the first and second ends 45, 47 of the link 43 within the third gap 51 as shown in FIGS. 7 and 8. The width of the second gap 41 between the first and second back members 33, 37 is at least equal to the width 75 of the first neck 71, and is preferably the greater than the width 75 of the first neck 71 and the full width of the second end 63 of the proximal femoral rasp/trial stem 13 for allowing the calcar collar 11 to fit around the proximal femoral rasp/trial stem 13 with portions of the second end 63 of the proximal femoral rasp/trial stem 13 located within the second gap 41 as clearly shown in FIG. 8. The depth of the fourth gap 53 between the first and second ends 45, 47 and the bight portion 49 of the link 43 is at least equal to the depth 73 of the of the first neck 71, and is preferably the same as the depth 73 plus a tolerance dimension for allowing the first neck 71 to fit within the fourth gap 53 as shown in FIG. 7. The width of the first gap 31 between the first and second foot members 23, 27 is preferably slightly less than the width 75 of the first neck 71 so that the first and second foot members 23, 27 must be slightly spread apart when the first neck 71 is inserted through the first gap 31 into or out of the third and fourth gaps 51, 53 as will now be apparent to those skilled in the art. The first neck 71 preferably has a substantially planar medial face 77 having relative sharp corners 79 for coacting with the corners 52 formed at the junction between the first and second foot members 23, 27 and the first and second ends 45, 47, respectively, of the link 43 to provide a snap-fit connection between the calcar collar 11 and the first neck 71 as will now be apparent to those skilled in the art and as shown in FIG. 7. The cross sectional shape and area of the first neck 71 is preferably smaller that the adjacent portions of the second end 63 of the proximal femoral rasp/trial stem 13 and the first neck 71 preferably has a certain height 81 as clearly shown in FIG. 5. The set dimension 59 between the first and second faces 55, 57 of the link 43 is no greater than to the height 81 of the of the first neck 71, and is preferably the same as the height 81, less a small tolerance dimension, for allowing the first neck 71 to receive the link 43 as shown in FIG. 8.

In addition, the proximal femoral rasp/trial stem 13 preferably includes at least a second groove or neck 83 adjacent the second end 69 and spaced from the first neck 71. The second neck 83, and any addition necks not shown, are preferably identical to the first neck 71 for allowing the calcar collar 11 to be snapped onto the proximal femoral rasp/trial stem 13 at different levels, and the above disclosure of the first neck 71 should be considered for a full and complete disclosure and understanding of the construction and function of the second neck 83, and any additional necks not shown. It should be noted that, if desired, the proximal femoral rasp/trial stem 13 may include three or more such grooves or stems to provide additional adjustability, etc., as will now be apparent to those skilled in the art.

The proximal femoral rasp/trial stem 13 may be constructed in various manners and out of various materials as will now be apparent to those skilled in the art. Thus, for example, the proximal femoral rasp/trial stem 13 is preferably forged, machined or otherwise constructed as a one-piece, integral unit out of a medical grade, physiologically acceptable metal such as stainless steel or the like, in various sizes to fit a range of typical patients and in various specific ornamental designs, etc.

The proximal femoral trial stem 15 may be substantially similar to any typical proximal femoral trial stem well know to those skilled in the art, having a first end 85 for inserting into a prepared socket S in a proximal femur F, and a second end 63 to which a proximal femoral trial head 88 can be attached (see FIG. 20) to perform a trial reduction of a hip joint, etc.

However, the proximal femoral trial stem 15 includes certain improvements to such a typical proximal femoral trial stem, and is especially designed and constructed for use in combination with the calcar collar 11. More specifically, the proximal femoral trial stem 15 has a first groove or neck 89 adjacent the second end 87 thereof for receiving the calcar collar 11. The first neck 89 is preferably identical to the first neck 71 of the proximal femoral rasp/trial stem 13 for allowing the calcar collar 11 to be snapped onto the proximal femoral trial stem 15 as will now be apparent to those skilled in the art. Thus, the first neck 89 has a cross-sectional shape with a certain depth 73 and width 75 as clearly shown in FIG. 10, a substantially planar medial face 95 having relative sharp corners 97 as clearly shown in FIG. 10, and a certain height 99 as clearly shown in FIG. 9. The above disclosure of the first neck 71 should be considered for a full and complete disclosure and understanding of the construction and function of the first neck 89 and the dimensional relationship between the various parts of the calcar collar 11 and the first neck 89, etc.

Likewise, the proximal femoral trial stem 15 preferably includes at least a second groove or neck 101 adjacent the second end 87 and spaced from the first neck 89. The second neck 101, and any addition necks not shown, are preferably identical to the first neck 89 for allowing the calcar collar 11 to be snapped onto the proximal femoral trial stem 15 at different levels, and the above disclosure of the first neck 89 should be considered for a full and complete disclosure and understanding of the construction and function of the second neck 101, and any additional necks not shown. It should be noted that, if desired, the proximal femoral trial stem 15 may include three or more such grooves or stems to provide additional adjustability, etc., as will now be apparent to those skilled in the art.

The proximal femoral trial stem 15 may be constructed in various manners and out of various materials as will now be apparent to those skilled in the art. Thus, for example, the proximal femoral trial stem 15 is preferably forged, machined or otherwise constructed as a one-piece, integral unit out of a medical grade, physiologically acceptable metal such as stainless steel or the like, in various sizes to fit a range of typical patients and in various specific ornamental designs, etc.

The method of preparing a proximal femur F for trial reduction of the present invention includes the step of exposing the proximal femur F in any desired manner now apparent to those skilled in the art. A typical bone saw 103 can then be used to make a transverse resection along a transverse plane 105 to form a transverse resection cut surface 107 on the proximal femur F, and to make a sagittal resection along a sagittal plane 109 to form a sagittal resection cut surface 111 on the proximal femur F (see, in general, FIGS. 13 and 14), thereby removing the head H and neck N of the proximal femur F, etc. If desired or necessary, a typical intramedullary reamer 113 may be used to cut an intramedullary bore 115 along the medullary cavity of the proximal femur F. If it is desired to use a proximal femoral trial stem 15 of the present invention for the trial reduction, a rasp is used to shape the socket S in the proximal femur F. Next, a specific calcar collar 11 and a specific proximal femoral stem of the present invention is provided and selected based on the size and shape of the proximal femur F, etc., and the selected calcar collar 11 is merely attached to the selected proximal femoral stem at a desired level by inserting a neck of the selected proximal femoral stem into the first gap 31 of the selected calcar collar 11 until the selected calcar collar 11 "snaps" onto the selected proximal femoral stem as will now be apparent to those skilled in the art. The first end of the selected proximal femoral stem is then inserted into the socket S of the proximal femur F with the face surfaces 35, 39 of the back members 33, 37 of the selected calcar collar 11 slidably contacting the sagittal resection cut surface 111 of the proximal femur F to guide the selected proximal femoral stem into the proximal femur F until the face surfaces 25, 29 of the foot members 23, 27 of the selected calcar collar 11 contacts the transverse resection cut surface 107 of the proximal femur F to stop the proximal femoral stem. When a combined proximal femoral rasp/trial stem 13 is used, the insertion step may include a number of back and forth partial insertions and removal to simultaneously form and shape the socket S in the proximal femur F and fully seat the proximal femoral rasp/trial stem 13 therein. After a successful trial reduction, the proximal femoral trial stem is removed from the proximal femur F and a permanent proximal femoral prosthesis (not shown) is implanted into the proximal femur F in any typical manner.

Although the present invention has been described and illustrated with respect to a preferred embodiment and a preferred use therefor, it is not to be so limited since modifications and changes can be made therein which are within the full intended scope of the invention.

We claim:

1. A calcar collar for a proximal femoral stem having a first end and a second end; the calcar collar comprising:

(a) a foot including a foot member having a face surface;

(b) a back attached to the foot and including a back member having a face surface arranged at an angle to the face surface of the foot member; and (c) attachment means for removably and adjustably attaching the foot and the back to the proximal femoral stem and for allowing the level of the face surface of the foot member to be varied between at least a first level located a first distance from the first end of the proximal femoral stem and a second level located a second distance from the first end of the proximal femoral stem.

2. A calcar collar for attachment to a proximal femoral stem; the calcar collar comprising:

(a) a foot including a first foot member having a planar face surface, and a second foot member having a planar face surface; the first and second foot members are spaced apart from one another to form a first gap;

(b) a back attached to the foot, including a first back member having a planar face surface arranged substantially at a right angle to the planar face surface of the first foot member, and including a second back member having a planar face surface arranged substantially at a right angle to the planar face surface of the second foot member; the first and second back members are spaced apart from one another to form a second gap; and (c) a link joining the first and second foot members together; the link including a first end joined relative to the first foot member, a second end joined relative to the second foot member, and a bight portion extending between the first and second ends thereof; the first and second ends of the link are spaced apart from one another to form a third gap; the third gap has a width that is greater than the first gap; the bight portion of the link extending from the first and second ends thereof to form a fourth gap; the link having a first face and a second face; the first and second faces of the link are spaced apart from one another a set distance.

3. A calcar collar for attachment to a proximal femoral stem having a first end for inserting into an intramedullary canal of the proximal end of a femur, a second end, and a neck adjacent the second end; the neck of the proximal femoral stem having a width, a depth, and a height; the calcar collar comprising:

(a) a foot including a first foot member having a planar face surface, and a second foot member having a planar face surface; the first and second foot members are spaced apart from one another a distance slightly less than the width of the neck of the proximal femoral stem to form a gap having a width slightly less than the width of the neck of the proximal femoral stem;

(b) a back attached to the foot, including a first back member having a planar face surface arranged substantially at a right angle to the planar face surface of the first foot member, and including a second back member having a planar face surface arranged substantially at a right angle to the planar face surface of the second foot member; the first and second back members are spaced apart from one another a distance at least equal to the width of the neck of the proximal femoral stem to form a gap having a width at least equal to the width of the neck of the proximal femoral stem; and (c) a link joining the first and second foot members together; the link including a first end joined relative to the first foot member, a second end joined relative to the second foot member, and an elastic bight portion extending between the first and second ends thereof;

the first and second ends of the link are spaced apart from one another a distance substantially the same as the width of the neck of the proximal femoral stem to form a gap having a width substantially the same as the width of the neck of the proximal femoral stem; the bight portion of the link extending from the first and second ends thereof a distance substantially the same as the depth of the neck of the proximal femoral stem to form a gap having a depth substantially the same as the depth of the neck of the proximal femoral stem; the link having a first face and a second face; the first and second faces of the link are spaced apart from one another a set distance substantially the same as the height of the neck of the proximal femoral stem.

4. The calcar collar of claim 3 in which the proximal femoral stem has a longitudinal axis extending through the neck thereof; in which the planar face surfaces of the first and second foot members are arranged substantially at right angles to the longitudinal axis of the proximal femoral stem; and in which the planar face surfaces of the first and second back members are arranged substantially parallel with the longitudinal axis of the proximal femoral stem.

5. In combination:
  (a) a proximal femoral stem having a first end for inserting into an intramedullary canal of the proximal end of a femur, a second end, a first neck adjacent the second end, and a second neck adjacent the second end and spaced from the first neck; each of the necks of the proximal femoral stem having a substantially identical width, depth, and height; and
  (b) a calcar collar attached to the proximal femoral stem; the calcar collar comprising:
    (i.) a foot including a first foot member having a planar face surface, and a second foot member having a planar face surface; the first and second foot members are spaced apart from one another a distance slightly less than the width of each of the necks of the proximal femoral stem to form a gap having a width slightly less than the width of each of the necks of the proximal femoral stem;
    (ii.) a back attached to the foot, including a first back member having a planar face surface arranged substantially at a right angle to the planar face surface of the first foot member, and a second back member having a planar face surface arranged substantially at a right angles to the planar face surface of the second foot member; the first and second back members are spaced apart from one another a distance at least equal to the width of each of the necks of the proximal femoral stem to form a gap having a width at least equal to the width of each of the necks of the proximal femoral stem; and
    (iii.) a link joining the first and second foot members together and removably and adjustably attaching the foot and the back to the proximal femoral stem; the link including a first end joined relative to the first foot member, a second end joined relative to the second foot member, and a bight portion extending between the first and second ends thereof and positioned around a portion of one of the necks of the proximal femoral stem; the first and second ends of the link are spaced apart from one another a distance substantially the same as the width of each of the necks of the proximal femoral stem to form a gap having a width substantially the same as the width of each of the necks of the proximal femoral stem; the bight portion of the link extending from the first and second ends thereof a distance substantially the same as the depth of each of the necks of the proximal femoral stem to form a gap having a depth substantially the same as the depth of each of the necks of the proximal femoral stem; the link having a first face and a second face; the first and second faces of the link are spaced apart from one another a set distance substantially the same as the height of each of the necks of the proximal femoral stem;

so that the calcar collar can be manually snapped into and out of each of the necks of the proximal femoral stem to thereby adjust the level of the planar faces surfaces of the first and second foot members relative to the proximal femoral stem.

6. The combination of claim 5 in which the proximal femoral stem is a proximal femoral trial stem.

7. The combination of claim 5 in which the proximal femoral stem is a proximal femoral rasp/trial stem.

8. A method of preparing a proximal femur for trial reduction, the method comprising the steps of:
  (a) exposing the proximal femur;
  (b) making transverse and sagittal resections on the proximal femur to provide a transverse resection cut surface and a sagittal resection cut surface on the proximal femur;
  (c) providing a proximal femoral stem having a first end for inserting into the intramedullary canal of the proximal end of the femur and a second end;
  (d) providing a calcar collar comprising a foot including a foot member having a face surface, and a back attached to the foot and including a back member having a face surface arranged at an angle to the face surface of the foot member;
  (e) attaching the calcar collar to the second end of the proximal femoral stem at a desired level; and then
  (e) inserting the first end of the proximal femoral stem into the intramedullary canal of the proximal femur with the face surface of the back member of the calcar collar slidably contacting the sagittal resection cut surface of the proximal femur to guide the proximal femoral stem into the intramedullary canal of the proximal femur until the face surface of the foot member of the calcar collar contacts the transverse resection cut surface of the proximal femur to stop the proximal femoral stem.

9. In combination:
  (a) a prosthetic stem having a first end for inserting into a bone, a second end opposite the first end, an exterior surface located between the first and second ends of the stem, a first groove in the exterior surface of the stem, and a second groove in the exterior surface of the stem a spaced distance toward the first end of the stem from the first groove; and
  (b) a collar comprising:
    (i.) a foot having a face surface;
    (ii.) a back attached to the foot and having a face surface; and
    (iii.) attachment means attaching the foot and back of the collar to the stem, the attachment means including means for engaging a selected one of the grooves in the exterior surface of the stem so that the collar can be attached to the stem relative to any selected one of the grooves in the exterior surface of the stem to thereby adjust the level of the face surface of the foot of the collar relative to the first and second ends of the stem.

* * * * *